(12) United States Patent
Staffel et al.

(10) Patent No.: US 8,110,700 B2
(45) Date of Patent: Feb. 7, 2012

(54) METHOD FOR PRODUCING VINYL ESTERS OF CARBOXYLIC ACIDS

(75) Inventors: Wolfgang Staffel, Waldsse (DE);
Roderich Roettger, Mannheim (DE);
Markus Christian Biel, Mannheim (DE); Reinhard Kaczmarek, Hassloch (DE)

(73) Assignee: BASF SE, Ludwigshafen (DE)

( * ) Notice: Subject to any disclaimer, the term of this patent is extended or adjusted under 35 U.S.C. 154(b) by 279 days.

(21) Appl. No.: 12/598,049

(22) PCT Filed: May 15, 2008

(86) PCT No.: PCT/EP2008/055945
§ 371 (c)(1),
(2), (4) Date: Oct. 29, 2009

(87) PCT Pub. No.: WO2008/138961
PCT Pub. Date: Nov. 20, 2008

(65) Prior Publication Data
US 2010/0152481 A1    Jun. 17, 2010

(30) Foreign Application Priority Data

May 16, 2007 (EP) ..................... 07108386

(51) Int. Cl.
*C07C 69/76* (2006.01)
*C07C 69/34* (2006.01)
*C07C 69/02* (2006.01)

(52) U.S. Cl. .......... 560/95; 560/113; 560/201; 560/231

(58) Field of Classification Search .................. None
See application file for complete search history.

(56) References Cited

U.S. PATENT DOCUMENTS

| 2,066,075 A | 12/1936 | Reppe |
| 3,455,998 A | 7/1969 | Arpe |
| 3,607,915 A | 9/1971 | Borsboom et al. |
| 5,387,569 A | 2/1995 | Shustorovich et al. |
| 5,395,960 A | 3/1995 | Heider et al. |
| 5,430,179 A | 7/1995 | Lincoln et al. |
| 5,525,316 A | 6/1996 | Shustorovich et al. |

FOREIGN PATENT DOCUMENTS

| EP | 0 512 656 | 11/1992 |
| EP | 0 622 352 | 11/1994 |
| WO | 93 16800 | 9/1993 |
| WO | WO 97/39006 A1 * | 10/1997 |

OTHER PUBLICATIONS

Hua, Ruimao et al., "Re (CO)$_5$Br-Catalyzed Addition of Carboxylic Acids to Terminal Alkynes: A High Anti-Markovnikov and Recoverable Homogeneous Catalyst", Journal of Organic Chemistry, vol. 69, pp. 5782-5784 (Jan. 1, 2004).

Mueller, T.E. et al., "Developing Transition-Metal Catalysts for the Intramolecular Hydroamination of Alkynes", Organometallics, vol. 19, pp. 170-183 (2000).

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for preparing vinyl carboxylates, wherein a carboxylic acid is reacted with an alkyne compound in the presence of a catalyst which is selected from salts of perrhenic acid at a temperature of =250° C.

The process gives rise to the desired vinyl esters with a high yield.

25 Claims, No Drawings

METHOD FOR PRODUCING VINYL ESTERS OF CARBOXYLIC ACIDS

The present invention relates to a process for preparing vinyl carboxylates by reacting a carboxylic acid with an alkyne.

The addition of carboxylic acids onto alkynes to prepare the corresponding vinyl carboxylates has been known for some time. Suitable catalysts used are especially zinc salts, such as the zinc salt of the carboxylic acid participating in the reaction; see, for example, U.S. Pat. No. 2,066,075, U.S. Pat. No. 3,455,998 and U.S. Pat. No. 3,607,915.

Since the zinc salts have only a low selectivity and stability, attempts have been made to use other catalysts. For instance, U.S. Pat. No. 5,430,179 describes the use of ruthenium complexes which are soluble in the reaction medium with a phosphine ligand. EP 512 656 A describes a process for preparing vinyl derivatives of Brønsted acids such as carboxylic acids by reacting the Brønsted acid with an acetylenically unsaturated compound in the presence of a ruthenium catalyst which has been applied to an inert porous support. J. Org. Chem. 2004, 69, 5782-5784 describes the reaction of terminal alkynes with acetic acid or benzoic acid using $Re(CO)_5Br$ as a catalyst. It has been found that the anti-Markovnikov adduct is obtained with high selectivity especially in n-heptane and toluene as solvents. Organometallics 2000, 19, 170-183 describes the intramolecular hydroamination of aminoalkyne compounds using $[Re(CO)_5(H_2O)]BF_4$ as a catalyst. However, only a low yield is obtained.

What is common to the prior art processes is that the yield of vinyl esters is unsatisfactory.

It is therefore an object of the present invention to provide a process for preparing vinyl carboxylates, which proceeds with a high yield.

Moreover, the process should be performable at temperatures at which even thermally labile carboxylic acids and vinyl carboxylates do not decompose.

Finally, the process should be performable with small amounts of catalyst in order to limit the costs of the catalyst.

It has now been found that, surprisingly, this object is achieved when the catalyst used comprises salts of perrhenic acid.

The present invention therefore provides a process for preparing vinyl carboxylates of the formula I:

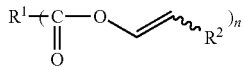   (I)

in which
a) $R^1$ is H or —COO—CH=CH—$R^2$ and n is 1,
b) $R^1$ is $C_1$-$C_{20}$-alkyl, $C_2$-$C_{20}$-alkenyl or $C_3$-$C_7$-cycloalkyl, and n is 1, 2 or 3, where $R^1$ is optionally substituted by 1, 2 or 3 radicals which are each independently selected from phenyl, halogen, hydroxyl, $C_1$-$C_4$-alkoxy, amino, mono-$C_1$-$C_4$-alkylamino, di-$C_1$-$C_4$-alkylamino, —OCOR$^3$, —COOR$^3$, —CONR$^4$R$^5$, —NR$^4$COR$^5$, —OCONR$^4$R$^5$ or —NR$^4$COOR$^5$, or
c) $R^1$ is aryl and n is 1, 2, 3, 4, 5 or 6, where aryl may optionally be substituted by 1, 2 or 3 radicals which are each independently selected from $C_1$-$C_4$-alkyl, halogen, hydroxyl, $C_1$-$C_4$-alkoxy, amino, mono-$C_1$-$C_4$-alkylamino, di-$C_1$-$C_4$-alkylamino, —OCOR$^3$, —COOR$^3$, —CONR$^4$R$^5$, —NR$^4$COR$^5$, —OCONR$^4$R$^5$ or —NR$^4$COOR$^5$; or $R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl;
$R^3$ is $C_1$-$C_4$-alkyl;
$R^4$ and $R^5$, which may be the same or different, are each H or $C_1$-$C_4$-alkyl;
comprising the reaction of a compound of the formula II

   (II)

in which $R^1$ is H or —COOH and n is 1 or $R^1$ has the definitions specified above under b), and n is 1, 2 or 3 or $R^1$ has the definitions specified above under c) and n is 1, 2, 3, 4, 5 or 6,
with a compound of the formula III

   (III)

in which $R^2$ has the definitions specified above, in the presence of a catalyst which is selected from salts of perrhenic acid at a temperature of ≦250° C.

Alkyl represents straight-chain or branched alkyl groups having the number of carbon atoms specified. Examples of such alkyl groups are methyl, ethyl, n-propyl, i-propyl, n-butyl, i-butyl, sec-butyl, t-butyl, n-hexyl, n-dodecyl, etc.

Examples of $C_2$-$C_{20}$-alkenyl groups are vinyl, 1- or 2-propenyl, buten-1-yl, buten-2-yl and isobutenyl.

Halogen is fluorine, chlorine, bromine or iodine.

Examples of $C_3$-$C_7$-cycloalkyl groups are cyclopropyl, cyclobutyl, cycloheptyl, and especially cyclopentyl and cyclohexyl.

Aryl is preferably phenyl or naphthyl.

When $R^1$ has the above-specified definition b), n is preferably 1 or 2.

When $R^1$ has the above-specified definition c), n is preferably 1, 2 or 3.

The catalysts used are one or more salts of perrhenic acid. Salts of perrhenic acid are compounds of the general formula $MReO_4$ and $M^1(ReO_4)_2$, where M is an inorganic or organic radical, such as Li, Na, K, $NH_4$, Ag(I), trialkyltin, triaryltin, tetraalkylammonium, and $M^1$ is an inorganic radical such as Ca, Mg, Ag(II). "Alkyl" and "aryl" are each as defined above. Examples are $LiReO_4$, $NaReO_4$, $NH_4ReO_4$, $Ca(ReO_4)_2$ and $AgReO_4$. $NH_4ReO_4$ is preferred.

The reaction is effected generally in the liquid phase. The catalyst can be used directly, for example in powder form, or applied to a support. Suitable supports are carbon powder, zeolites, aluminum oxides, silicon oxides, etc.

In general, the catalyst is used in an amount of from 0.000 005 to 1 mol %, preferably from 0.000 05 to 0.5 mol %, more preferably from 0.000 01 to 0.1 mol % and especially from 0.001 to 0.05 mol %, based in each case on equivalents of the compound of the formula II. The expression "equivalents" is based here on carboxyl groups of the formula II which can react with the compound of the formula III.

Suitable starting compounds of the formula II are aliphatic monocarboxylic acids. Examples of such carboxylic acids are formic acid, acetic acid, halogenated carboxylic acids such as chloroacetic acid, trifluoroacetic acid, propionic acid, aminocarboxylic acids such as alanine, lactic acid, butyric acid, hydroxycarboxylic acids such as hydroxybutyric acid, valeric acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propylheptanoic acid, pivalic acid, neononanoic acid, neodecanoic acid, neotridecanoic acid, stearic acid, oleic acid, lauric acid, palmitic acid, cyclohexanecarboxylic acid, acrylic acid, methacrylic acid, crotonic acid, cinnamic acid or phenylacetic acid.

Suitable starting compounds of the formula II are also aliphatic polycarboxylic acids, especially dicarboxylic acids, and the partly esterified and partly amidated derivatives of the polycarboxylic acids. Examples of aliphatic polycarboxylic acids are oxalic acid, malonic acid, succinic acid, glutaric acid, adipic acid, sebacic acid, agaric acid, 1,2,3-propanetricarboxylic acid, cyclohexane-1,2-dicarboxylic acid, cyclohexane-1,3-dicarboxylic acid, cyclohexane-1,4-dicarboxylic acid, citric acid, malic acid, tartaric acid, glutamic acid, maleic acid and fumaric acid, particular preference being given to the use of adipic acid.

Suitable starting compounds of the formula II are also aromatic monocarboxylic acids and polycarboxylic acids, and the partly esterified and partly amidated derivatives of the polycarboxylic acids. Examples of such carboxylic acids are benzoic acid, 2-, 3- or 4-methylbenzoic acid, salicylic acid, 2-, 3- or 4-aminobenzoic acid, 4-dimethylamino-benzoic acid, phthalic acid, isophthalic or terephthalic acid, 1,2,3-benzenetricarboxylic acid, 1,2,4-benzenetricarboxylic acid, 1,3,5-benzenetricarboxylic acid, 1,2,4,5-benzenetetracarboxylic acid, 1,2,3,4-benzenetetracarboxylic acid, benzenepentacarboxylic acid and benzenehexacarboxylic acid, and the derivatives of the polycarboxylic acids which have been esterified partly with a $C_1$-$C_4$-alkanol.

Suitable starting compounds of the formula III are, for example, acetylene, propyne, 1-butyne, 1-pentyne, 1-hexyne and phenylacetylene, particular preference being given to using acetylene.

The ratio of compound of the formula II to compound of the formula III can be selected within a wide range. In general, though, an excess of compound of the formula III, especially an excess of from 0.1 to 20 mol %, based on the compound of the formula II, is used.

The reaction is generally performed in a suitable inert solvent. If the compound of the formula II is liquid at the temperature employed, it is also possible to dispense with a solvent. Suitable inert solvents are aliphatic and aromatic hydrocarbons such as pentane, hexane, heptane, decalin, paraffin oil, toluene, xylene, etc., ethers such as tetrahydrofuran, dioxane, anisole or diphenyl ether, chlorinated hydrocarbons such as methylene chloride, 1,2-dichloroethane or chlorobenzene, esters such as ethyl acetate, n-butyl acetate or butyrolactone, acetonitrile, dimethylformamide, dimethyl sulfoxide, N-methylpyrrolidone or polyethylene glycols or mixtures thereof. The reaction may also be performed in a compound of the formula I as a solvent if it is liquid at the selected reaction temperature.

The reaction temperature can be selected freely within a wide range and is generally selected such that rapid reaction occurs without starting compounds or the product decomposing. In general, the temperature is in the range from 70 to 300° C., especially from 100 to 260° C., preferably from 140 to 220° C., from 150 to 210° C., from 160 to 210° C. and especially from 180 to 210° C.

The reaction is typically performed under pressure, the pressure set being preferably from 1 to 30 bar (absolute), preferably from 2 to 20 bar and especially from 5 to 25 bar or from 10 to 20 bar. The pressure can be set, for example, with the compound of the formula III employed and/or an inert gas such as nitrogen. The reaction time is generally in the range from 0.5 to 72 hours, especially from 1 to 48 hours.

If appropriate, it is also possible to add reaction-promoting additives, such as zinc acetate, lithium salts, for example LiCl, Lewis acids such as $BF_3$, etc., Lewis bases such as triethylamine, pyridine, 1,5-diazabicyclo[4.3.0]non-5-ene, etc.

Suitable reaction-promoting additives are also compounds which are capable of forming carbon monoxide under the reaction conditions. Examples thereof are formic acid, $C_1$-$C_6$-alkyl formates, oxalic acid, mono- or di-$C_1$-$C_6$-alkyl oxalates and formamide, which form carbon monoxide at the reaction temperatures contemplated here.

Suitable reaction-promoting additives are also compounds which act coordinatively on the rhenium, such as compounds having at least two OH groups or $C_1$-$C_4$-alkoxy groups. These include especially glycols, polyglycols, and compounds having a poly-$C_1$-$C_4$-alkyleneoxy chain, and the etherified derivatives thereof. Examples thereof are ethylene glycol, polyethylene glycols such as diethylene glycol or triethylene glycol, 1,2- or 1,3-propylene glycol, poly-1,2-propylene glycols, poly-1,3-propylene glycols, 1,2-, 1,3- or 1,4-butylene glycol, or the corresponding polybutylene glycols and the corresponding glycol ethers, such as dimethylethylene glycol, dimethyldiethylene glycol, etc., alkoxylated, especially ethoxylated and/or propoxylated, fatty alcohols and the derivatives thereof which have been etherified with a $C_1$-$C_4$-alkyl group.

The reaction-promoting additives are used generally in at least 10-fold molar excess based on the catalyst. Appropriately, the additives are used in a from 10- to 100 000-fold molar excess. If the reaction-promoting additive used is a carbon monoxide-forming compound, it is used appropriately in a from 10- to 10 000-fold excess, based on the catalyst.

The reaction can be performed batchwise, continuously or in a semibatchwise process. The workup is effected in a customary manner, appropriately by distilling off the vinyl carboxylate desired. The catalyst remains in the bottoms and can, if appropriate, be reused. Appropriately, the reaction and the workup, especially the purifying distillation, can be performed in the presence of a polymerization inhibitor. The polymerization inhibitors used may, for example, be hydroquinone, hydroquinone monomethyl ether, 2,5-di-t-butylhydroquinone, 2,6-di-t-butyl-p-cresol, nitroso compounds such as isoacryloyl nitrate, nitrosodiphenylamine, N-nitrosocyclohexylhydroxylamine, methylene blue, phenothiazine, tannic acid or diphenylamine. The polymerization inhibitors are used generally in amounts of from 1 to 10 000 ppm, especially from 100 to 1000 ppm, based in each case on the overall mixture.

The reaction proceeds selectively, i.e., even in the presence of other vinylatable groups in the compound of the formula II, such as OH or $NH_2$, only the carboxyl groups are vinylated. If a compound of the formula II is used which, as well as the carboxyl group(s), also comprises another vinylatable group, the reaction temperature is appropriately selected within the range from 100 to 220° C. and/or the reaction time within the range from 0.5 to 12 hours.

In a preferred embodiment, the invention relates to a process for preparing vinyl carboxylate compounds of the formula I:

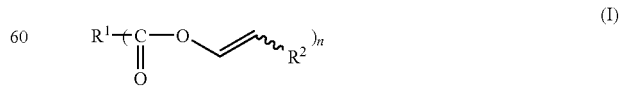

in which
a) $R^1$ is H or —COO—CH=CH—$R^2$ and n is 1,
b) $R^1$ is $C_1$-$C_{20}$-alkyl, $C_2$-$C_{20}$-alkenyl or $C_3$-$C_7$-cycloalkyl, and n is 1, 2 or 3, where $R^1$ is optionally substituted by 1 or 2 radicals which are each independently selected from phenyl, halogen and $C_1$-$C_4$-alkoxy, or
c) $R^1$ is aryl and n is 1, 2, 3, 4, 5 or 6, where aryl may optionally be substituted by 1, 2 or 3 radicals which are each independently selected from $C_1$-$C_4$-alkyl, halogen and $C_1$-$C_4$-alkoxy;

$R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl;

by reacting a compound of the formula II

in which $R^1$ is H, —COOH or the definitions specified above under b) or c), and n has the definitions specified above, with a compound of the formula III

in which $R^2$ has the definitions specified above, in the presence of a catalyst which is selected from salts of perrhenic acid at a temperature of =230° C.

A preferred embodiment of the invention relates to the reaction of the compounds of the formula II in which $R^1$ is H, $C_1$-$C_6$-alkyl, $C_3$-$C_7$-cycloalkyl or phenyl, where the alkyl group may be substituted as specified above under b) and the phenyl group as specified above under c), and n is 1, with acetylene.

A further preferred embodiment relates to the reaction of the compounds of the formula II in which $R^1$ is $CO_2H$ and n is 1, or in which $R^1$ is $C_1$-$C_{20}$-alkyl, especially $C_1$-$C_4$-alkyl, where $R^1$ may be substituted as specified under b) and n is 2, with acetylene. Preference is given to performing this reaction at a temperature in the range from 70 to 230° C., especially from 60 to 220° C. or from 180 to 210° C. The catalyst is used especially in an amount of from 0.001 to 0.5 mol %, especially from 0.01 to 0.1 mol %, based on equivalents of dicarboxylic acid. The reaction of adipic acid with acetylene is particularly preferred.

A further preferred embodiment relates to the reaction of the compounds of the formula II in which $R^1$ is phenyl which may be substituted as specified above under c), and n is 2, 3, 4, 5 or 6, especially 2 or 3, with acetylene. Preference is given to performing this reaction at a temperature in the range from 140 to 230° C., especially from 150 to 220° C. The catalyst is used preferably in an amount of from 0.001 to 0.1 mol %, especially from 0.01 to 0.1 mol %, based on equivalents of polycarboxylic acid.

Preference is given to the preparation of the compounds of the formula I

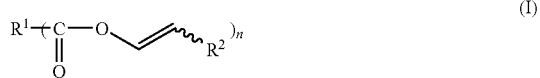

in which $R^1$ is aryl and n is 2, 3, 4, 5 or 6, where aryl may optionally be substituted by 1, 2 or 3 radicals which are each independently selected from $C_1$-$C_4$-alkyl, halogen, $C_1$-$C_4$-alkoxy, amino, mono-$C_1$-$C_4$-alkylamino, di-$C_1$-$C_4$-alkylamino, —$OCOR^3$, —$COOR^3$, —$CONR^4R^5$, —$NR^4COR^5$, —$OCONR^4R^5$ or —$NR^4COOR^5$; or $R_1$ is $C_3$-$C_7$-cycloalkyl and n is 2 or 3; and $R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl.

Particular preference is given to the preparation of divinyl phthalate, divinyl terephthalate and divinyl isophthalate, and of cyclohexane 1,2-divinyl ester, cyclohexane 1,3-divinyl ester and cyclohexane 1,4-divinyl ester.

The vinyl esters obtainable by the process according to the invention are suitable for use in materials which can be cured thermally or by high-energy radiation. The materials may be used as or in coating materials, for example coatings, printing inks or adhesives, as printing plates, as moldings, for producing photoresists, in stereolithography or as a casting composition, for example for optical lenses. Substrates for coating may, for example, be textile, leather, metal, plastic, glass, wood, paper or paperboard. The compounds of the formula I can be used as crosslinkers in free-radical and cationic polymerizations. They are preferably used in UV-curable coatings, for example as reactive diluents.

The examples which follow illustrate the invention without restricting it. The GC analyses (GC: gas chromatography) were effected on a capillary column with a carbowax (polyethylene glycol) film, for example DB Wax from J & W Scientific.

EXAMPLES

Example 1

A mixture of 45.0 g (308 mmol) of adipic acid, 25 mg of $NH_4ReO_4$ (0.093 mmol) and 105 ml of xylene was subjected to vinylation at 200° C., a nitrogen pressure of 2 bar and an acetylene pressure of 18 bar for 8 h. Divinyl adipate was detectable as the main product by means of GC analysis.

Example 2

A mixture of 45.0 g (308 mmol) of adipic acid, 10 mg of $NH_4ReO_4$ (0.037 mmol) and 105 ml of xylene was subjected to vinylation at 200° C., a nitrogen pressure of 2 bar and an acetylene pressure of 18 bar for 8 h. Divinyl adipate was detectable as the main product by means of GC analysis.

Example 3

A mixture of 60.0 g (411 mmol) of adipic acid, 25 mg of $NH_4ReO_4$ (0.093 mmol) and 90 ml of xylene was subjected to vinylation at 200° C., a nitrogen pressure of 2 bar and an acetylene pressure of 18 bar for 8 h. Divinyl adipate was detectable as the main product by means of GC analysis.

Example 4

A mixture of 60.0 g (411 mmol) of adipic acid, 25 mg of $NH_4ReO_4$ (0.093 mmol) and 90 ml of xylene was subjected to vinylation at 200° C., a nitrogen pressure of 2 bar and an acetylene pressure of 18 bar for 8 h. Divinyl adipate was detectable as the main product by means of GC analysis.

Example 5

A mixture of 60.0 g (411 mmol) of adipic acid, 25 mg of $NH_4ReO_4$ (0.093 mmol), 1.0 g (9.8 mmol) of tert-butyl formate and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 6

A mixture of 60.0 g (411 mmol) of adipic acid, 25 mg of $NH_4ReO_4$ (0.093 mmol), 0.5 g (10.8 mmol) of formic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 7

A mixture of 60.0 g (411 mmol) of adipic acid, 25 mg of $NH_4ReO_4$ (0.093 mmol), 0.5 g (10.8 mmol) of formic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 8

A mixture of 60.0 g (411 mmol) of adipic acid, 25 mg of $NH_4ReO_4$ (0.093 mmol), 0.5 g (8.62 mmol) of methyl formate and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 9

A mixture of 60.0 g (411 mmol) of adipic acid, 25 mg of $NH_4ReO_4$ (0.093 mmol), 0.5 g (5.5 mmol) of oxalic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 10

A mixture of 60.0 g (411 mmol) of adipic acid, 15 mg of $NH_4ReO_4$ (0.056 mmol), 0.3 g (3.3 mmol) of oxalic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 11

A mixture of 60.0 g (411 mmol) of adipic acid, 15 mg of $NH_4ReO_4$ (0.056 mmol), 0.3 g (6.5 mmol) of formic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 12

A mixture of 60.0 g (411 mmol) of adipic acid, 15 mg of $NH_4ReO_4$ (0.056 mmol), 0.1 g (2.2 mmol) of formic acid and 90 ml of xylene was subjected to vinylation at 200° C., a nitrogen pressure of 2 bar and an acetylene pressure of 18 bar for 6 h. Divinyl adipate was detectable as the main product by means of GC analysis.

Example 13

A mixture of 60 g (411 mmol) of adipic acid, 15 mg of $NH_4ReO_4$ (0.056 mmol), 0.26 g (5.7 mmol) of formic acid and 90 g of xylene (isomer mixture) was subjected to vinylation at 200° C., a nitrogen pressure of 2 bar and an acetylene pressure of 18 bar for 6 h. Divinyl adipate was detectable as the main product by means of GC analysis.

Example 14

A mixture of 60 g (411 mmol) of adipic acid, 10 mg of $NH_4ReO_4$ (0.015 mmol), 0.17 g (3.70 mmol) of formic acid, 45 g of xylene (isomer mixture) and 45 g of Plurafac LF 131 (ethoxylated fatty alcohol) was subjected to vinylation at 200° C., a nitrogen pressure of 2 bar and an acetylene pressure of 18 bar for 6 h. Divinyl adipate was detectable as the main product by means of GC analysis.

Example 15

A mixture of 600.0 g (4.11 mol) of adipic acid, 100 mg of $NH_4ReO_4$ (0.373 mmol), 3.0 g (65 mmol) of formic acid and 900 g of xylene (isomer mixture) was subjected to vinylation at 200° C., a nitrogen pressure of 2 bar and an acetylene pressure of 18 bar for 6 h. The divinyl adipate yield determined by means of GC was 91%.

Example 16

A mixture of 600.0 g (4.11 mol) of adipic acid, 80 mg of $NH_4ReO_4$ (0.298 mmol), 3.0 g (65 mmol) of formic acid and 900 g of xylene (isomer mixture) was subjected to vinylation at 200° C., a nitrogen pressure of 2 bar and an acetylene pressure of 18 bar for 6 h. The divinyl adipate yield determined by means of GC was 89%.

Example 17

A mixture of 1000.0 g (6.85 mol) of adipic acid, 100 mg of $NH_4ReO_4$ (0.373 mmol), 1.8 g (39 mmol) of formic acid and 1500 g of xylene (isomer mixture) was subjected to vinylation at 190° C., a nitrogen pressure of 2 bar and an acetylene pressure of 18 bar for 6 h. A conversion of >98% was found by means of GC analysis. The main product was divinyl adipate.

Example 18

A mixture of 1000.0 g (6.85 mol) of adipic acid, 50 mg of $NH_4ReO_4$ (0.187 mmol), 0.9 g (20 mmol) of formic acid and 1500 g of xylene (isomer mixture) was subjected to vinylation at 190° C., a nitrogen pressure of 2 bar and an acetylene pressure of 18 bar for 6 h. The divinyl adipate yield determined by means of GC was 71%.

Example 19

A mixture of 1000.0 g (6.85 mol) of adipic acid, 80 mg of $NH_4ReO_4$ (0.298 mmol), 2.88 g (63 mmol) of formic acid and 1500 g of xylene (isomer mixture) was subjected to vinylation at 190° C., a nitrogen pressure of 2 bar and an acetylene pressure of 18 bar for 6 h. The divinyl adipate yield determined by means of GC was 87%.

Example 20

A mixture of 1000.0 g (6.85 mol) of adipic acid, 70 mg of $NH_4ReO_4$ (0.261 mmol), 2.5 g (54 mmol) of formic acid and 1500 g of xylene (isomer mixture) was subjected to vinylation at 190° C., a nitrogen pressure of 2 bar and an acetylene pressure of 18 bar for 6 h. The divinyl adipate yield determined by means of GC was 83%.

Example 21

A mixture of 1000.0 g (6.85 mol) of adipic acid, 100 mg of NH$_4$ReO$_4$ (0.373 mmol), 2.6 g (57 mmol) of formic acid and 1500 g of xylene (isomer mixture) was subjected to vinylation at 190° C., a nitrogen pressure of 2 bar and an acetylene pressure of 18 bar for 6 h. The divinyl adipate yield determined by means of GC was 83%. A conversion of >98% was found by means of GC analysis. The main product was divinyl adipate.

Example 22

A mixture of 60.0 g (0.41 mol) of adipic acid, 15 mg of NH$_4$ReO$_4$ (0.055 mmol), 0.26 g (5.7 mmol) of formic acid and 90 g of anisole was subjected to vinylation at 200° C., a nitrogen pressure of 2 bar and an acetylene pressure of 18 bar for 6 h. A conversion of >98% was found by means of GC analysis. The main product was divinyl adipate.

Example 23

A mixture of 60.0 g (0.41 mol) of adipic acid, 15 mg of NH$_4$ReO$_4$ (0.055 mmol), 0.26 g (5.7 mmol) of formic acid and 90 g of diglyme was subjected to vinylation at 200° C., a nitrogen pressure of 2 bar and an acetylene pressure of 18 bar for 6 h. A conversion of >98% was found by means of GC analysis. The main product was divinyl adipate.

Example 24

A mixture of 60.0 g (0.41 mol) of adipic acid, 15 mg of NH$_4$ReO$_4$ (0.055 mmol), 0.26 g (5.7 mmol) of formic acid and 90 g of Plurafac LF 131 was subjected to vinylation at 180° C., a nitrogen pressure of 2 bar and an acetylene pressure of 18 bar for 6 h. A conversion of >98% was found by means of GC analysis. The main product was divinyl adipate.

The invention claimed is:

1. A process for preparing vinyl carboxylate compounds of the formula I:

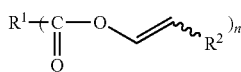
(I)

in which
a) R$^1$ is H or —COO—CH=CH—R$^2$ and n is 1,
b) R$^1$ is C$_1$-C$_{20}$-alkyl, C$_2$-C$_{20}$-alkenyl or C$_3$-C$_7$-cycloalkyl, and n is 1, 2 or 3, where R$^1$ is optionally substituted by 1, 2 or 3 radicals which are each independently selected from phenyl, halogen, hydroxyl, C$_1$-C$_4$-alkoxy, amino, mono-C$_1$-C$_4$-alkylamino, di-C$_1$-C$_4$-alkylamino, —OCOR$^3$, —COOR$^3$, —CONR$^4$R$^5$, —NR$^4$COR$^5$, —OCONR$^4$R$^5$ or —NR$^4$COOR$^5$, or
c) R$^1$ is aryl and n is 1, 2, 3, 4, 5 or 6, where aryl may optionally be substituted by 1, 2 or 3 radicals which are each independently selected from C$_1$-C$_4$-alkyl, halogen, hydroxyl, C$_1$-C$_4$-alkoxy, amino, mono-C$_1$-C$_4$-alkylamino, di-C$_1$-C$_4$-alkylamino, —OCOR$^3$, —COOR$^3$, —CONR$^4$R$^5$, —NR$^4$COR$^5$, —OCONR$^4$R$^5$ or —NR$^4$COOR$^5$;

R$^2$ is H, C$_1$-C$_8$-alkyl, phenyl-C$_1$-C$_4$-alkyl, phenyl which is optionally substituted by 1 or 2 C$_1$-C$_4$-alkyl groups, or C$_3$-C$_7$-cycloalkyl;
R$^3$ is C$_1$-C$_4$-alkyl;
R$^4$ and R$^5$, which may be the same or different, are each H or C$_1$-C$_4$-alkyl;
comprising the reaction of a compound of the formula II

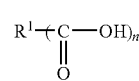
(II)

in which R$^1$ is H or —COOH and n is 1 or R$^1$ has the definitions specified above under b) and n is 1, 2 or 3 or R$^1$ has the definitions specified above under c) and n is 1, 2, 3, 4, 5 or 6,
with a compound of the formula III

(III)

in which R$^2$ has the definitions specified above, in the presence of a catalyst which is selected from one or more salts of perrhenic acid at a temperature of ≦250° C.

2. The process according to claim 1, wherein the catalyst is NH$_4$ReO$_4$.

3. The process according to claim 1, wherein the catalyst is used in an amount in the range from 0.000 005 to 1 mol %, based on equivalents of the compound of formula II.

4. The process according to claim 1, wherein the compound of formula III is selected from acetylene, propyne, 1-butyne, 1-pentyne, 1-hexyne and phenylacetylene.

5. The process according to claim 1, wherein the compound of formula II is an aliphatic monocarboxylic acid.

6. The process according to claim 5, wherein the aliphatic monocarboxylic acid is selected from acetic acid, phenylacetic acid, propionic acid, alanine, butyric acid, hydroxybutyric acid, valeric acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propylheptanoic acid, pivalic acid, neononanoic acid, neodecanoic acid, neotridecanoic acid, stearic acid, oleic acid, lauric acid, palmitic acid, cyclohexanecarboxylic acid, acrylic acid, methacrylic acid, crotonic acid and cinnamic acid.

7. The process according to claim 1, wherein the compound of formula II is an aliphatic dicarboxylic acid.

8. The process according to claim 7, wherein the aliphatic dicarboxylic acid is selected from malonic acid, succinic acid, glutaric acid, adipic acid, maleic acid and fumaric acid.

9. The process according to claim 8, wherein the compound of formula II is adipic acid.

10. The process according to claim 1, wherein the compound of formula II is a cycloaliphatic mono- or dicarboxylic acid.

11. The process according to claim 10, wherein the compound of formula II is cyclohexane-1,2-dicarboxylic acid, cyclohexane-1,3-dicarboxylic acid or cyclohexane-1,4-dicarboxylic acid.

12. The process according to claim 7, wherein the reaction is performed at a temperature in the range from 70 to 260° C.

13. The process according to claim 10, wherein the reaction is performed at a temperature in the range from 70 to 260° C.

14. The process according to claim 7, wherein the catalyst is used in an amount in the range from 0.000 01 to 0.1 mol %, based on equivalents of the compound of formula II.

15. The process according to claim 10, wherein the catalyst is used in an amount in the range from 0.00001 to 1.0 mol %, based on equivalents of the compound of formula II.

16. The process according to claim 1, wherein the compound of formula II is an aromatic monocarboxylic acid or an aromatic polycarboxylic acid.

17. The process according to claim 16, wherein the compound of formula II is benzoic acid, phthalic acid, isophthalic acid or terephthalic acid.

18. The process according to claim 16, wherein the reaction is performed at a temperature in the range from 140 to 230° C.

19. The process according to claim 1, wherein the compound of formula III is used in an excess of from 0.1 to 20 mol %, based on equivalents of the compound of formula II.

20. The process according to claim 1, wherein the compound of formula III is acetylene.

21. The process according to claim 1, wherein the reaction is performed in the presence of one or more reaction-promoting additives.

22. The process according to claim 21, wherein the reaction-promoting additive is a carbon monoxide-forming compound.

23. The process according to claim 22, wherein the carbon monoxide-forming compound is formic acid, $C_1$-$C_6$-alkyl formates, oxalic acid, mono-$C_1$-$C_6$-alkyl oxalates, di-$C_1$-$C_6$-alkyl oxalates or formamide.

24. The process according to claim 23, wherein the reaction-promoting additive is a glycol or a glycol $C_1$-$C_4$-alkyl ether.

25. The process according to claim 24, wherein the reaction-promoting additive is a poly-$C_2$-$C_4$-alkylene glycol or a compound having a poly-$C_2$-$C_4$-alkylene glycol chain.

* * * * *